(12) United States Patent
Carta

(10) Patent No.: US 8,192,767 B2
(45) Date of Patent: Jun. 5, 2012

(54) ANTIOXIDANT COMPOSITIONS COMPRISING EXTRACTS OF MYRTLE AND ROSEMARY

(75) Inventor: Angelico Carta, Pula (IT)

(73) Assignee: Nuraging Biotech S.R.L., Pula (Cagliari) (IT)

( * ) Notice: Subject to any disclaimer, the term of this patent is extended or adjusted under 35 U.S.C. 154(b) by 128 days.

(21) Appl. No.: 12/376,363

(22) PCT Filed: Jul. 24, 2007

(86) PCT No.: PCT/EP2007/057605
§ 371 (c)(1),
(2), (4) Date: Oct. 8, 2009

(87) PCT Pub. No.: WO2008/015127
PCT Pub. Date: Feb. 7, 2008

(65) Prior Publication Data
US 2010/0227002 A1    Sep. 9, 2010

(30) Foreign Application Priority Data

Aug. 4, 2006  (IT) .............................. RM2006A0427

(51) Int. Cl.
*A01N 65/00*    (2009.01)
(52) U.S. Cl. ....................................................... 424/725
(58) Field of Classification Search .................. None
See application file for complete search history.

(56) References Cited

U.S. PATENT DOCUMENTS

2002/0051826 A1  5/2002  Darland et al.

FOREIGN PATENT DOCUMENTS

| BE | 1 106 041 A6 | 2/2006 |
| SU | 1 030 407 A | 7/1983 |
| TR | 9 902 067 A2 | 4/2001 |

OTHER PUBLICATIONS

Database WPI Week 198530, Derwent Publications Ltd., London, GB; AN 1985-182293 & SU 1 030 407 A (Yaloveny Eng Cons) Jul. 23, 1983 abstract.
Brühl; "Genussvolier Abschluss" Getränkefachgrosshandel, [Online] 1996, pp. 753-758.
Database EPODOC European Patent Office, The Hague, NL; TR9902067 abstract & TR 9 902 067 A2 (Kurtsan Iiaciari A S [TR]) Apr. 20, 2001.
Etter S C: Rosmarinus officinalis as a antioxidant, Journal of Herbs, Spices and Medicinal Plants, Food products press, Bingham, NY, US, vol. 11, No. 1-2, 2004, pp. 121-159.
Hras Andreja Rizner et al.: "Comparison of antioxidative and synergistic effects of rosemary extract with alph-tocopherol, ascorbyl palmitate and citric acid in sunflower oil", Food Chemistry, vol. 71, No. 2, Nov. 1, 2000, pp. 229-233. ISSN: 0308-8146.
Database CA Chemical Abstracts Service, Columbus, Ohio, US; 2004, Romani et al.: "Evaluation of antioxidant effect of different extracts of *Myrtus communis* L", Database accession No. 2004: 140578 abstract & Free Radical Research Jan. 2004, vol. 38, No. 1, Jan. 2004, pp. 97-103, ISSN: 1071-5762.
Romani A. et al.; "Identification and quantitation of polyphenols in leaves of *Myrtus communis* L.", Chromatographia 1999, Germany, vol. 49, No. 1-2, 1999, pp. 17-20, ISSN: 0009-5893.
Hadafi A, et al.; "Application de la technique d'hemolyse a la mise en evidence du pouvoir antioxidant des extraits aromatiques du romarin, myrte et ciste; (Asseeement of antioxidant activity of extracts of herbs . . . )", Rivista Italiana Eppos, Istituto Thetrahedron, Milan, IT, 1998, pp. 314-324, ISSN: 03920-0445.
Harris R.: "Synergism in the Essential Oil World", International Journal of Aromatherapy, Aromatherapy Publications, Hove, GB, vol. 12, No. 4, 2002, pp. 179-186, ISSN: 0962-4562, p. 6.
"News", Internet Article, [Online] Sep. 26, 2006.
"NRA-Nuragin", Internet Article, [Online], Jan. 2007.
Abraham R. et al.: "Cyclic GMP is a Second Messenger by which Nitric Oxide Inhibits Diaphragm Contraction", Comp. Biochem. Physiol. vol. 119A. No. 1, pp. 177-183, 1998.
Ames B, et al.: "Oxidants, antioxidants, and the degenerative diseases of aging", Proc. Natl. Acad. Sci. USA, vol. 90, pp. 7915-7922, Sep. 1993.
Andrade F, et al.: "Effect of nitric oxide on single skeletal muscle fibers from the mouse", Journal of Physiology (1998), 509.2. pp. 577-586.
Baubr G: "Reactive Oxygen and Nitrogen Species: Efficient, Selective, and Interactive Signals, During Intercellular Induction of Apoptosis", Anticancer Research 20.4115-4140 (2000).
Clanton T. et al. "Oxidants and Skeletal Muscle Function: Physiologic and Pathophysiologic Implications", Society for Experimental Biology and Medicine, 1999.
Cree I. et al.: "Measurements of Cytotoxicity by ATP-based Luminescence Assays in Primary Cell Cultures and Cell Lines", Toxicology in Vitro 11 (1997) 553-556.
Ehara S, et al.: "Elevated Levels of Oxidized Low Density Lipoprotein Show a Positive Relationship with the Severity of Actue Coronary Syndromes", Circulation—Journal of the American Heart Association, 2001: 103: 1955-1960.
Galinier A, et al. "Adipose Tissue Proadipogenic Redox Chanages in Obesity", The Journal of Biological Chemistry, vol. 281, No. 18, pp. 12682-12687, May 5, 2006.
Grassmann J, et al.: "Antioxidant Properties of Essential Oils—Possible explanations for their anti-inflammatory effects", Argneim.-Forsch/Drug Res. 50 (I), Nr. 2 (2000).
Guan S. et al.: "Protective effect of protocatechuic acid from *Alpinia oxyphylla* on hydrogen preroxide-induced oxidative PC12 cell death", European Journal of Pharmacology 538 (2006) 73-79.
Hengartner M: "The biochemistry of apoptosis", Nature vol. 407, Oct. 12, 2000, pp. 770-776.
Jialal I, et al.: "The Effect of alpha-Tocopherol Supplementation of LDL Oxidation: A Dose-Response Study", Arteriosclerosis, Thrombosis, and Vascular Biology, vol. 15(2) Feb. 1995, pp. 190-198.

(Continued)

*Primary Examiner* — Michael Meller
(74) *Attorney, Agent, or Firm* — Knobbe, Martens, Olson & Bear, LLP

(57) ABSTRACT

The invention relates to a composition based on extracts of myrtle and rosemary which has been found to synergistically increase the protection of cells against pathophysiological conditions characterised and partly caused by overproduction of free radicals and to counteract the oxidative stress caused by excessive production of said free radicals, as well as for preventing and/or treating related pathologies, including apoptosis.

15 Claims, 9 Drawing Sheets

OTHER PUBLICATIONS

Keusch G, et al.: "Nutrition and Infection", Ann. Rev. Nutr. 1986. 6:131-54.

Kwon Y, et al.: "Redox Regulation of Cell Growth and Cell Death", Biol. Chem., vol. 384, pp. 991-996, Jul. 2003.

Lo A., et al.: "Carnosol, an antioxidant in rosemary, suppresses inducible nitric oxide synthase though down-regulating nuclear factor-kB in mouse macrophages", Carcinogenesis, vol. 23, No. 6, pp. 983-991, 2002.

Maeda H, et al.: "Nitric Oxide and Oxygen Radicals in Infection, Inflammation, and Cancer", Biochemistry 1998 vol. 63(7): 854-65

Mancinelli R, et al.: "Functional role of inducible nitric oxide synthase on mouse colonic motility", Neuroscience Letters 311 (2001) p. 101-104.

Mates J, et al.: "Antioxidant Enzymes and their Implications in Pathophysiologic Processes", Frontiers in Bioscience 4, d339-345, Mar. 15, 1999.

Nicholson D: "From bench to clinic with apoptosis-based therapeutic agents", Nature, vol. 407, pp. 810-816, Oct. 12, 2000.

Rand M: "Nitrergic Transmission: Nitric Oxide as a Mediator of Non-Adrenergic, Non-Cholinergic Neuro-Effector Transmission", Clinical and Experimental Pharmacology and Physiology (1992) 19, 147-169.

Reid M: "Plasticity in Skeletal, Cardiac, and Smooth Muscle, Invited Review: Redox modulation of skeletal muscle contraction: What we know and what we don't", J. Appl. Physiol, 90:724-731, 2001.

Reid M, et al.: "N-Acetylcysteine Inhibits Muscle Fatigue in Humans", J. Clin. Invest., vol. 94, Dec. 1994, 2468-2474.

Rossetti Z, et al.: "Biphasic effects of NMDA on the motility of the rat portal vein", British Journal of Pharmocology (2000) 129, 156-162.

Stähelin H: "The Impact of Antioxidants on Chronic Disease in Ageing and in Old Age", Int. J. Vitam. Nutr. Res., 69 (3), 1999, 146-149.

Travaline J, et al.: "Effect of N-Acetylcysteine on Human Diaphragm Strength and Fatigability", American Journal of Respiratory and Critical Care Medicine, 1997, 156:1567-1571.

Wiseman H, et al.: "Damage to DNA by reactive oxygen and nitrogen species: role in inflammatory disease and progression to cancer", Biochem. J. (1996) 313, 17-29.

Zeng H. et al.: "Antioxidant properties of phenolic diterpenes from *Rosmarinus officinalis*", Acta Pharmacol Sin, Dec. 22, 2001, 22 (12), 1094-1098.

International Search Report dated Jul. 24, 2007, for International Application No. PCT/EP2007/057605.

Bendich, Adrianne: "Antioxidant Vitamins and Human Immune Responses", Vitamins and Hormones, vol. 52, Human Nutrition Research, Hiffmenn-La Roche Inc., Paramus, pp. 35-43, New Jersey 07652, 1996.

Harman D: "Towards Prolongation of the Healthy Life Span: Practical Approaches to Intervention", Annals of the New York Academy of Sciences, vol. 854, pp. xxiii-xiv & 1-5, published online Feb. 7, 2006.

Stadtman T: "Selenium Biochemistry. Mammalian Selenoenzymes", Annals of New York of Sciences, pp. 399-402, published online Jan. 25, 2006.

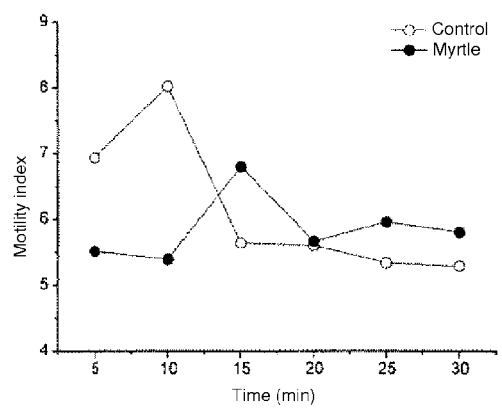
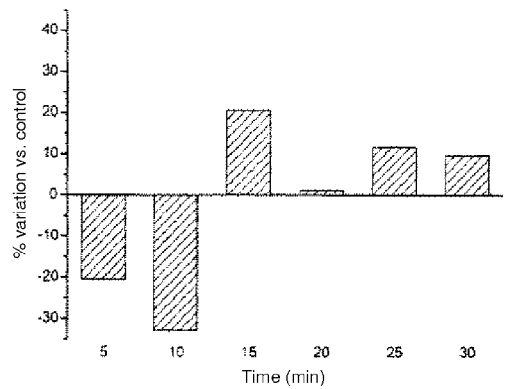
Fig. 7 A
Fig. 7 B
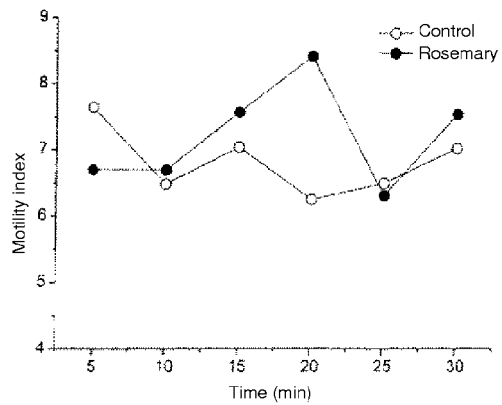
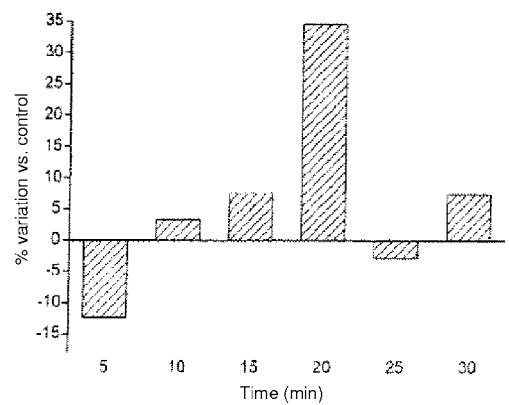
Fig. 8 A
Fig. 8 B

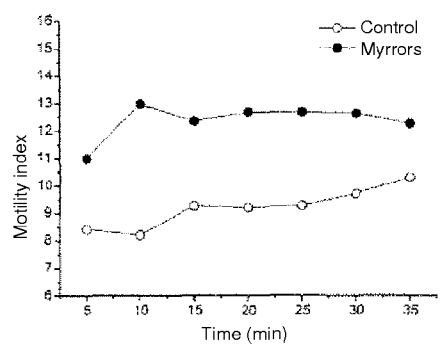
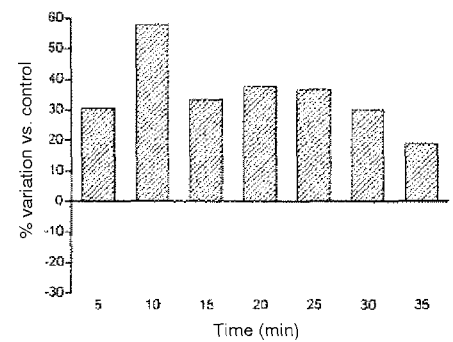
Fig. 9 A  Fig. 9 B
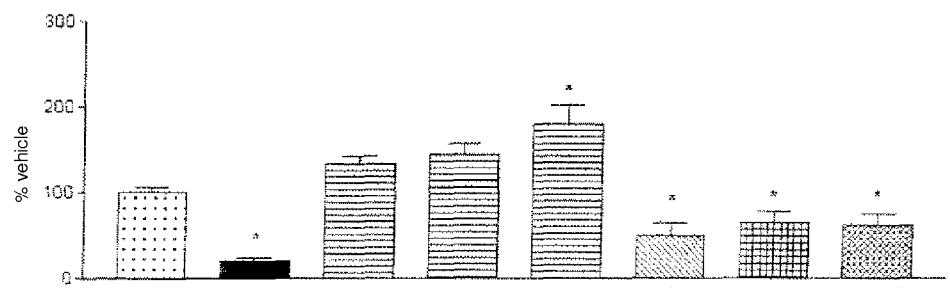
Fig. 10

ANTIOXIDANT COMPOSITIONS COMPRISING EXTRACTS OF MYRTLE AND ROSEMARY

This application is U.S. National Phase of International Application PCT/EP2007/057605, filed Jul. 24, 2007 designating the U.S., and published in English as WO 2008/015127 on Feb. 7, 2008, which claims priority to Italian Patent Application No. RM2006A000427, filed Aug. 4, 2006.

FIELD OF THE INVENTION

The present invention relates to antioxidant compositions comprising extracts of rosemary and myrtle to be used to prepare medicaments for treatment and prevention of disorders and diseases related to the overproduction of free radicals.

According to another aspect of the invention, said extracts are used with the same purpose to prepare health foods, nutraceuticals, dermatological and cosmetic products and drugs to be used in veterinary medicine.

PRIOR ART

The protective action afforded by antioxidants in counteracting oxidative stress is well known [(*Towards Prolongation of healthy life span*—Ann. N.Y. Acad. Sci., 854, (1998), New York (edited by Harman D.; Holliday R. and M. Meydany); Stahlin H. B., *The Impact of Antioxidants on Chronic Disease in Aging and Old Age*—Int. J. Vitamin Nutr. Res. 69, 146-149; (1999)].

Free radicals are also well known as oxidants and are of endogenous origin (related to biological processes in the body) or exogenous origin deriving from pollution, nutrition, exposure to the sun's rays and general conditions of life.

The main mechanisms whereby free radicals, not effectively counteracted by the antioxidant system, are able to cause pathological conditions are lipid peroxidation; mutagenic action on DNA; apoptosis; uncontrolled proteolysis, and immune dysfunction [Kwon Y. W., Masutani H., Nakamura H., Ishii Y., Yodoi J. *Redox regulation of cell growth and cell death*—Biol. Chem. 384 (7): 991-996; (2003)]. In particular, apoptosis is a physiological cell death mechanism which permits the cell turnover of tissues. Many of the agents that induce apoptosis are oxidants or activators of cellular oxidative metabolism and many substances capable of inhibiting apoptosis are antioxidants. This suggests a crucial role of free radicals in the regulation of programmed cell death [Hengartner M. G: *The biochemistry of apoptosis*—Nature 407, 770-775; (2000)].

Apoptosis induced by free radicals also plays an important pathogenetic role in numerous disease conditions and in aging itself [Nicholson D. W.-*From bench to clinic with apoptosis-based therapeutic agents* Nature 407, 810-816; (2000)].

The combination of oxidative damage due to endogenous and exogenous causes gives rise to alterations in the structure of tissues and in their function which manifest themselves as aging, chronic degenerative diseases (e.g. arthritis), atherosclerosis and cancer [Ames B. N., Shigenaga M. K., Hagen T. M. *Oxidants, antioxidants, and the degenerative diseases of aging*—Proc. Natl. Acad. Sci. (USA) 90: 7915, (1993)], as in the case of gastrointestinal cancer, cancer of the prostate and breast, cerebral degenerative diseases and diseases of the cerebrovascular system.

Antioxidants can be helpful for cardiovascular function in the following ways:
Detoxifying cholesterol [Ehara S. Circulation; 103: (2001); Jialal I. *Thrombosis and Vascular Biology* 15(2): 190-98 (1995)];
Counteracting chronic inflammation, responsible, amongst other things, for possible occlusion of the arteries, heart attacks and infarcts;
Improving vascular functions through a dilating and anti-inflammatory action on the endothelium of the arteries;
Counteracting coagulation of the blood (antiplaque action). Immunohistochemical and biochemical evidence demonstrates the significant role of the reactive oxygen species (ROS) of the body in acute and chronic inflammation. Factors contributing to the cytotoxic effect of ROS are the early phases of lipid peroxidation, direct inhibition of the enzymatic chain of mitochondrial respiration, inactivation of glyceraldehyde-3-phosphate dehydrogenase, inhibition of cell membrane $Na^+/K^+$ ATP-ase activity, inactivation of sodium membrane channels and modification of other oxidative proteins. All these toxicities play a role in shock pathology, inflammation and reperfusion.

Blood flow is influenced by the acute and chronic inflammation that affects a multiplicity of organs and manifests itself in a multiplicity of symptoms, the most common being pain. Other diseases which may be related to oxidative damage are: asthma, diabetes, obesity, depression, heart conditions, arthritis, Alzheimer's disease, osteoporosis and other age-related diseases [Maeda H., Akaike T. *Nitric oxide and oxygen radicals in infection, inflammation, and cancer*—Biochemistry 63: 854-865 (1998); Wiseman H., Halliwell B. *Damage to DNA by reactive oxygen and nitrogen species; role in inflammatory disease and progression to cancer*—Biochem. J. 313:17-29; (1996)]; chronic diseases such as chronic fatigue syndrome, fibromyalgia, heavy metal toxicity, infections in general, irritable bowel syndrome. Crohn's disease [Bauer G. *Reactive oxygen and nitrogen species: Efficient, selective, and interactive signals during intercellular induction of apoptosis*—Anticancer Res. 20:4115-4139; (2000)]; diabetes mellitus (diabetes Types I and II) and related syndromes, particularly the inability to synthesise antioxidant enzymes [Mates J. M., Sanchez-Jimenez F. *Antioxidant enzymes and their implications in pathophysiologic processes*—Front Biosci 4: 339-345; (1999)]; vitamin C deficiency and scurvy.

Other metabolic disorders, such as obesity, mitochondrial diseases and "metabolic syndrome" itself appear to be related to increased levels of ROS, such as the enzyme NADPH oxidase [Galinier et al., *Adipose Tissue Proadipogenic Redox Changes in Obesity*—J. Biol. Chem. 281: 12682-12687; (2006)].

Denutrition and malnutrition are the underlying cause of alterations of the immune response, with consequent:
Deficient immune defences, particularly a greater predisposition to many viral infections, for example, due to rotavirus, measles virus and parainfluenza virus [Scrimshaw N. S, *Nutrition and infection*—Prog. Food Nutr. Sci. 1: 393-420: (1975); Harbige L. S, *Nutrition and immunity with emphasis on infection and autoimmune disease*—Nutr. Health 10: 285-312; (1996)];
Alteration of the antibody response, which, for example, manifests itself in the form of reduced activity of macrophages and T cell dysfunctions [Bendich A. *Antioxidant vitamins and human immune responses*—Vit. Horm. 52: 35-62; (1996); Stadtman T. C. *Selenium bio*-

*chemistry. Mammalian selenoenzymes*—Ann. N.Y. Acad. Sci. 899: 399-402; (2000)].

The effects of ROS and of nitric oxide (NO) derivatives have also been evaluated in the physiological modulation of skeletal and smooth muscle contractile functions [Balon T. W. *Integrative biology of nitric oxide and exercise*—Exerc. Sport Sci, Rev, 27: 219-253; (1999); Clanton T. L. et al., *Oxidants and skeletal muscle functions: physiologic and pathophysiologic implications*—Proc. Soc. Exp. Biol. Med. 222: 253-262; (1999)]. The biological oxidant activity of ROS in skeletal muscle is counterbalanced by that exerted by a series of endogenous antioxidants. Important in this connection is the modulatory role exerted by NO, which is capable, at low concentrations (in resting muscle), of offsetting the effect of ROS both directly and through the induction of a second cascade of redox-active derivatives, capable in turn of exercising an antioxidant action [Abraham R. Z. et al., *Cyclic GMP is a second messenger by which nitric oxide inhibits diaphragm contraction*—Comp. Biochem. Physiol. 119A: 177-183; (1998); Andrade F. H. et al., *Effect of nitric oxide on single skeletal muscle fibers from the mouse*—J. Physiol. (Lond) 509:577-586, (1998)].

On the contrary, high concentrations of NO (which are registered during the contractile activity of the muscle) interact with the superoxide anion inducing frank pro-oxidant activity [Balon T. W. *Integrative biology of nitric oxide and exercise*—Exerc. Sport Sci. Rev. 27: 219-253; (1999)].

It would thus seem clear that the balance between ROS and NO and its derivatives in skeletal muscle is of particular importance for proper functioning of the muscle, manifesting itself clinically in an acute, direct manner on the sense of fatigue, and indirectly and chronically on the aging processes of muscle fibre itself.

NO depresses the production of contractile force in non-fatigued skeletal muscle, exerting a similar action on the myocardium and on the smooth muscle of various organs [Reid M. B. *Plasticty in skeletal, cardiac and smooth muscle*—J. Appl. Physiol. 90: 724-731; (2001)].

At smooth muscle level the observations reported on the motility of isolated rat portal vein are of interest [Rossetti Z. L. et al., *Biphasic effect of NMDA in the rat portal vein*—Br. J. Pharmacol. 129:156-162; (2000)], where it is postulated that the biphasic modulatory effect of NMDA on portal vein smooth muscle may be exerted through activation of the NO modulatory system, as also observed previously [Rand M. J. *Nitrergic transmission: nitric oxide as a mediator of non-adrenergic, non-cholinergic neuro-effector transmission*—Clin. Exp. Pharmacol. Physiol. 19: 147-169; (1992)].

The use of a number of exogenous antioxidants utilised as dietary supplements has proved useful in inhibiting muscle fatigue in human subjects [Reid M. B. et al. *N-acetylcysteine inhibits muscle fatigue in humans*—J. Clin. Invest. 94: 2468-2474; (1994); Travaline J. M. et al., *Effect of N-acetylcysteine on human diaphragm strength and fatigue*—Am. J. Resp. Crit. Care Med. 156: 1567-1571; (1997)].

All the above-mentioned metabolic disorders and/or alterations can be treated or prevented al least in part by means of therapies based on active ingredients containing antioxidants.

Rosemary (*Rosmarinus officinalis*, Labiatae) is an ubiquitous plant in the Mediterranean area and is characterised by antioxidant and antimicrobial pharmacological properties.

The main components of the rosemary phytocomplex are:
Essential oil: alpha-pinene; 1,8-cineol; borneol, camphene, limonene, linalool, isobutyl acetate, 3-octanone, terpineol, verbenol;
Flavonoids: apigenin, diosmetin, diosmin, genkwanin, 6-methoxygenkwanin, hispidulin, sinensetin, luteolin;
Rosmarinic acid and other phenolic acids
Diterpenes: picrosalvin, carnosol, carnosolic acid and rosmariquinone;
Other components such as rosmaricin, ursolic acid and oleanolic acids.

It has been demonstrated in vitro and in vitro that the antioxidant activity of the *Rosmarinus officinalis* phytocomplex is mainly due to the presence of carnosol, carnosic acid and rosmarinic acid [Ai-Hsiang Lo et al., *Carnosol, an antioxidant in rosemary, suppresses inducibile nitric oxide synthase through down-regulating nuclear factor-kB in mouse macrophages*—Carcinogenesis 23, 6: 983-991; (2002); Zeng H. H. et al., *Antioxidant properties of phenolic diterpenes from Rosmarinus officinalis*—Acta Pharmacol. Sin. 22, 12: 1094-1098; (2001)]. This activity is also related to the anti-inflammatory and chemopreventive action of rosemary.

Myrtle (*Myrtus communis*, Myrtaceae) is the only member of this family present in Europe, while all the others are to be found in Australia and in the tropics. Myrtle is used in popular medicine for its astringent, tonic, disinfectant and balsamic properties.

The main components of the phytocomplex, extracted from the leaves and berries, are the essential oil, non-prenylated acylfluoroglycinols, flavonoids, phenolic acids and terpenes. Also present is alpha-tocopherol. The essential oil from myrtle leaves and fruits contains 27 components, the main ones being alpha-pinene, 1,8-cineol and limonene. Non-prenylated acylfluoro-glycinols are represented by the compounds myrtucommulone and semimyrtucommulone. The flavonoids of myrtle are mainly represented by quercetin and myrcetin. The phenolic acids are mostly gallic acid, ellagic acid and tannins [Grassman J. et al., *Antioxidant properties of essential oils. Possible explanations for their anti-inflammatory effects*—Arzneimittelforschung 50; 2: 135-139; (2000)].

To date, studies and assays have been conducted with extracts of myrtle or rosemary, or their antioxidant components assayed singly.

It has now been found that a combination of the dry extracts of these two plants, i.e. *Rosmarinus officinalis* and *Myrtus communis* exerts a synergistic action, revealing the reciprocal enhancement of the antioxidant activities of each extract, which proves extremely useful for achieving a highly efficacious protective effect on human and animal cells.

In addition, the combination of the two extracts has surprisingly been shown to be capable of significantly enhancing their effects on isolated smooth muscle motility as compared to the results obtained with the same substances administered singly. In particular, the effects induced by the combination of the two extracts appear to be characterised by a marked positive enhancement of muscular inotropism.

As stated above, the function and motility of skeletal muscle and smooth muscle seem to be directly modulated by the cellular redox equilibrium, with an acute effect on muscle fatigue and a chronic effect on inflammatory processes and on the aging processes of the muscle fibre itself.

Lastly, of great importance then was the unexpected observation of marked anti-apoptotic activity induced by the combination of the two extracts when administered on cell cultures of pheochromocytoma PC12 stressed by means of the presence of $H_2O_2$ in the culture medium. This surprising result would appear to be at least partly attributable to the marked synergistic antioxidant activity displayed by the combination of the two extracts.

SUMMARY OF THE INVENTION

The aim of the present invention is therefore to improve cell protection based on the synergistic combination of extracts of the plants rosemary and myrtle, as well as the use of this combination for the treatment or prevention of pathological conditions related to overproduction of free radicals due to exogenous or endogenous causes of the human or animal organism. According to the invention, the composition can be utilised to prepare drugs for the treatment and prevention of disorders and diseases related to the overproduction of free radicals; in addition it can be used with the same purpose to prepare health foods, nutraceuticals, dermatological and cosmetic products and to prepare medicaments to be used also in veterinary medicine.

Another object of the invention is to provide a composition comprising a combination of pharmaceutically effective doses of:
a) extracts of leaves of rosemary as claimed in the claims attached hereto;
b) extracts of leaves of myrtle as claimed in the claims attached hereto;
possibly in combination with adjuvants, excipients, dispersing agents, and other active ingredients with a known pharmacological action.

Another object of the invention is the process for the preparation of compositions, comprising a mixing stage of the two extracts and subsequent modalities for obtaining the various types of formulations, to be selected in the group of granules, powders, pills, suppositories, suspensions, solutions, creams, pastes and syrups.

Yet another object of the invention consists in the mode of administration, which may be oral, topical, parenteral or transdermic. Further objects will be clear from the following detailed description of the invention.

BRIEF DESCRIPTION OF THE FIGURES

FIG. 7. Single substance formulation. Effect on portal vein contractility. Control vs. myrtle. (A) motility index, (B) % variation vs. control.

FIG. 8. Single substance formulation. Effect on portal vein contractility. Control vs. rosemary. (A) motility index, (B) % variation vs. control.

FIG. 9. Coformulation of myrtle and rosemary (so-called myrros). Effect on portal vein contractility (A) motility index (B) % variation vs. control.

FIG. 10. Effect of myrtle extract on ATP production of rat PC12 cells after toxicity induced by $H_2O_2$ FIG. 11. Effect of rosemary extract on ATP production of rat PC12 cells after toxicity induced by $H_2O_2$ FIG. 12. Effect of the combination of the extracts of myrtle and rosemary: protection of rat PC12 cells against the reduction in ATP induced by $H_2O_2$.

DETAILED DESCRIPTION OF THE INVENTION

Figure 1:
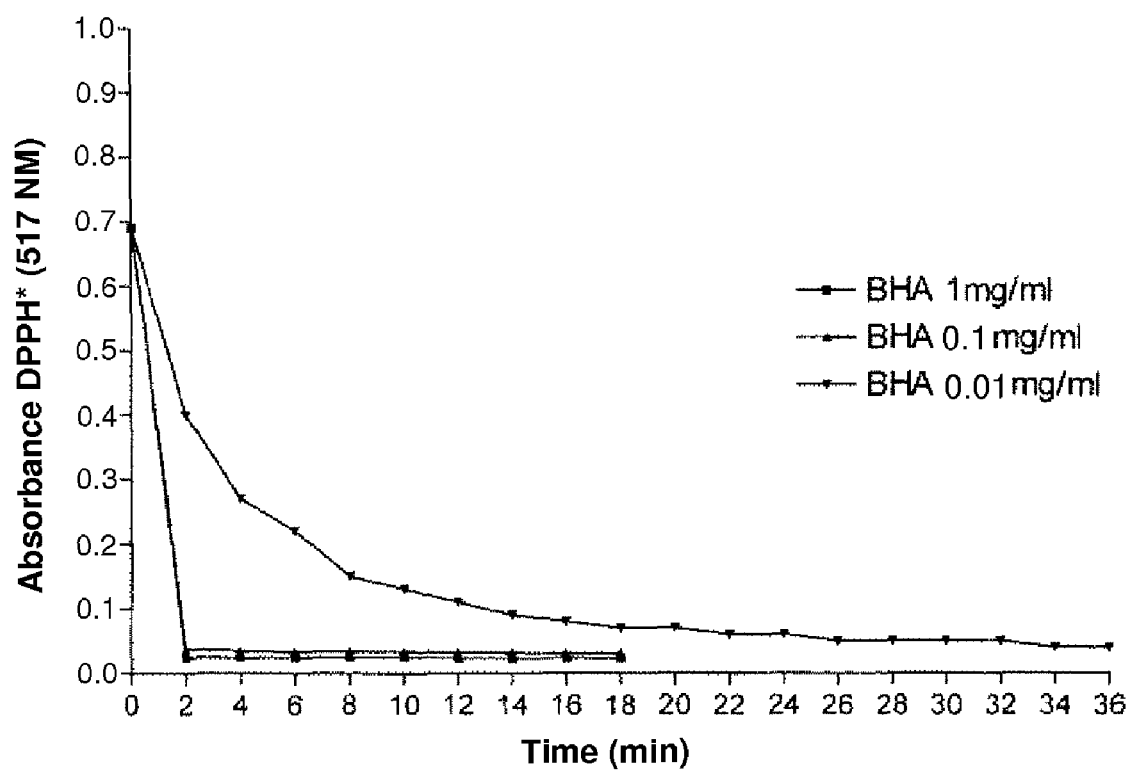
FIG. 1. Reference concentrations of butylated hydroxy anisol (BHA) as standard antioxidant. Reduction of absorbance of DPPH* as a function of time in the presence of the standard antioxidant BHA at the concentrations of 1, 0.1, and 0.01 mg/ml.

The object of the invention is the surprising finding that administration of the combination of the extracts of the plants rosemary and myrtle significantly increases, in a synergistic manner, cell protection against the oxidative damage tested according to the antiradical DPPH procedure. The results obtained in the experimental studies described demonstrate that the cell protection-enhancing activity achieved with the combination of the above-mentioned substances is significantly greater than that of the single extracts. This synergistic effect was detected by combining extracts of various types (obtained with various solvents, such as, for example, aqueous, alcoholic, hydroalcoholic and apolar aprotic solvents). Experts in the field are familiar with the various types of extracts.

A further object of the invention, directly related to the first one described, is the surprising finding that administration of the combination of dry extracts of the plants rosemary and myrtle induces a marked positive enhancement of muscular inotropism as tested on the isolated rat portal vein.

A further object of the invention, once again related to the cell protection against the damage induced by biological oxidation phenomena, is the surprising observation that the administration of dry extracts of the plants myrtle and rosemary induces a marked anti-apoptotic activity in rat pheochromocytoma PC12 cell cultures, apoptosis being expressed as a reduction in the concentration of ATP induced by the administration of hydrogen peroxide ($H_2O_2$).

The invention as a whole then relates to a positive synergistic combination of natural extracts of myrtle and rosemary in order to improve protection of cells against pathophysiological conditions characterised and partly caused by overproduction of free radicals and to counteract the oxidative stress caused by excessive production of said free radicals, and to prevent and/or treat the related diseases and disorders.

Said enhanced protection is based on the administration of effective amounts of compositions capable of exerting a protective or curative activity, containing synergistic quantities, of the order of doses ranging from 1 mg to 1000 mg of each of the extracts of myrtle and rosemary prepared as indicated here below.

The extracts according to the present invention can be obtained by means of the extraction processes known to the expert in the field, starting from leaves as gathered, or preferably by treating dried leaves. Extraction processes in which the leaves are ground before being subjected to the extraction stage are to be preferred. To this end the leaves of myrtle or rosemary are separated from the plants and naturally dried in order to eliminate all the water present in them and to obtain the maximum yield during the extraction. The next step after drying is preferably a grinding step to obtain an easier penetration of the solvent in the vegetable tissues.

The extracts of myrtle and rosemary are obtained by treating the leaves with a solid/liquid extraction process to be selected, for example, from among: Soxhlet extraction, maceration, percolation, ultrasound, or by vapour distillation or by extraction with supercritical fluids. These processes are conducted using a (weight-by-weight) vegetal matrix:solvent ratio ranging from 1:1 to 1:50 and for time periods ranging from 30 minutes to 45 days. The extracts thus obtained may then be subsequently rectified to increase the purity of the extracts through liquid/liquid extraction or by passage on suitable chromatography columns or SPE (solid phase extraction).

The solvents used are those normally used in the context of the extraction of vegetal substances and can be selected from among the group consisting of water, hydroalcohol solutions, polar organic solvents such as alcohols, ketones, ethers, esters; apolar aprotic organic solvents such as hydrocarbon solvents and carbon dioxide. Acetone, ethylene glycol, propylene glycol, diethylether, petroleum ether, ethyl acetate and methylene chloride, for example, can be used.

The extracts, obtained according to the methods indicated above are used to obtain compositions comprising:
a) myrtle extract, particularly starting from the leaves of *Myrtus communis*;
b) rosemary extract, particularly starting from the leaves of *Rosmarinus officinalis*;
the combination of a) and b) being characterised by an antioxidant potency at least 5% greater than the sum of the antioxidant potencies of the single components at the same concentrations; preferably 15% greater; more preferably, in the range from 16 to 50%, as measured with the DPPH test in ethanol at the wavelength of 517 nm as described here below.

Preferably used are:
a) myrtle extract, particularly *Myrtus communis*, produced starting from dried leaves and characterised by a reference antioxidant action observed with the DPPH test and expressed as the ability to inhibit the absorbance of DPPH by 50% ($EC_{50}$) in a concentration range from 110 to 175 mcg/ml.
b) rosemary extract, particularly *Rosmarinus officinalis* produced starting from dried leaves and characterised by a reference antioxidant action observed with the DPPH test and expressed as $ED_{50}$ in a concentration range from 5 to 35 mcg/ml.

Preferably the weight-by-weight ratio (a):(b) should range from 0.1:1000 to 1000:0.1 for myrtle and rosemary, respectively.

The compositions according to the invention can be used in the pharmaceutical or cosmetic fields or can be used in the field of nutrition as dietary supplements or as nutraceuticals or as health foods. The compositions are formulated in such a way that the active ingredient is present in daily doses consisting of:
from approximately 1 mg to 1000 mg of rosemary extract;
from approximately 1 mg to 1000 mg of myrtle extract;
with a weight-by-weight ratio between the two components ranging from 0.1:1000 to 1000:0.1 for myrtle and rosemary, respectively.

The compositions according to the invention preferably further comprises, as is known to any expert in the pharmaceutical field, excipients (the most appropriate for the administration and nutritional route preselected), vitamins, such as, for example, the B, C and E vitamin complex, mineral salts, amino acids, antioxidants, coenzymes, such as coenzyme Q10, magnesium, zinc, lutein, alpha-lipoic acid, chondroitin, glucosamine, gingko biloba, and phosphatidylserine.

The compositions can be formulated and exert their preventive action, whether in the form of a dietary supplement or cosmetic or that of an actual drug, in the prevention and treatment of pathological conditions related to overproduction of free radicals in animals and humans. The administration and dosage will depend upon the support or preventive or strictly therapeutic action one intends to exert and according to the particular subjects to whom the compositions and formulations are to be administered.

The compositions and formulations can be prepared in solid, semisolid or liquid form, in the form of tablets, lozenges, pills, capsules, granules, syrups, ampoules, drops, emulsions, suspensions, creams or gels.

In the context of the present invention, compositions are preferred in which the extracts are: extract from dried leaves of *Myrtus communis*, extract from dried leaves of *Rosmarinus officinalis*, each of which possibly in an amount ranging from approximately 1 mg to 1000 mg.

The compositions can be administered orally in the form of a dietary supplement; or via parenteral, rectal or transdermic routes in the form of a pharmaceutical preparation; or topically in the form of a cosmetic preparation.

The compositions can be used as dietary supplements or as cosmetics or as drugs for the prevention and/or treatment of the oxidative stress caused by overproduction of free radicals and for the prevention and/or treatment of related disorders and disease conditions, such as aging, neurodegenerative diseases, atherosclerosis, chronic inflammation, metabolic disorders, cancer, viral infections, skin aging, chronic fatigue and acute muscle fatigue, aging of muscle fibres, digestive tract disorders, dyspepsia, biliary and intestinal transit disorders, liver metabolism disorders, obesity, and for the control of weight and body mass.

Experiments conducted with a combination of the extracts according to the present invention and using the most significant assays in relation to the therapeutic or preventive action anticipated for the combination have surprisingly revealed a potent synergistic antioxidant effect of the composition which is the object of the present invention.

The antioxidant activity of the combination which is the object of the present invention can be assayed in vitro using the DPPH (2,2-diphenyl-1-picryl-hydrazyl) spectrophotometric method. This method makes it possible to determine the antioxidant potential of a molecule to be assayed by measuring the variation of the absorbance of the radical DPPH in its presence at the wavelength of 517 nm (as reported in the literature) [Blois M. S., *Antioxidant determination by the use of a stable free radical*—Nature, 181:1199-1200; (1958)], according to the reaction:

$$Z \cdot + AH = ZH + A \cdot \quad [1]$$

where:
Z· is the radical DPPH
AH is the single antioxidant (reducing) molecule present in the composition or in the extract
ZH is the reduced form of DPPH
A· is the free radical produced by oxidation of the antioxidant molecule.

The greater the reduction of the absorbance of the radical DPPH in solution, the greater will be the antioxidant potential of the molecule studied. The final results of the assay are expressed as $EC_{50}$, i.e. as the concentration of antioxidant molecule at which there is a 50% reduction of the DPPH radical according to the following formula:

$A(T_0)$=absorbance of the control sample at time 0
$A(T_n)$=absorbance in the presence of the antioxidant sample at time n.

The antioxidant capacity of the combination according to the present invention was assayed in ethanol, using a DPPH concentration of $6.0 \times 10^{-6}$ M and final concentrations of each extract, previously solubilised in ethanol, ranging from 1 mcg/ml to 3 mg/ml. For the purposes of evaluating the synergistic effect the extracts were also assayed in a mixture in ratios ranging from 0.1:1 to 9.9:1. The myrtle and rosemary extracts were each subjected to the same extraction procedure, selected from among those indicated above, then brought to dryness and redissolved in ethanol at the desired concentrations so as to standardise the evaluation methodology. The absorbance was then determined at the wavelength of 517 nm in 1 cm quartz cells.

Figure 6:
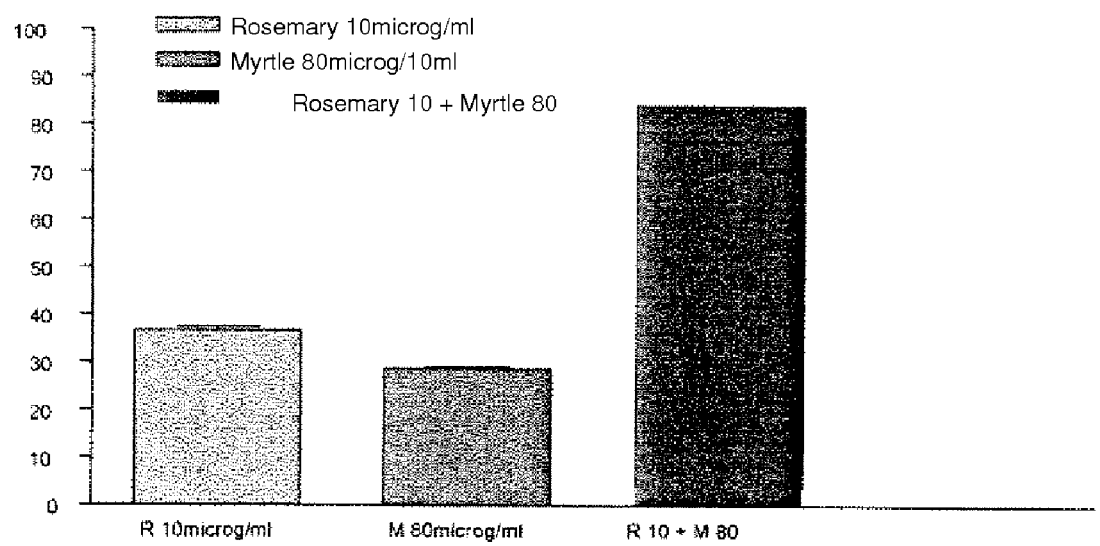
FIG. 6. Synergistic antioxidant effect of the combination of myrtle and rosemary. Antioxidant action obtained by the extracts of rosemary and myrtle tested singly and in combination. The data are expressed as % inhibition of the absorbance of DPPH*.
Figure 11:
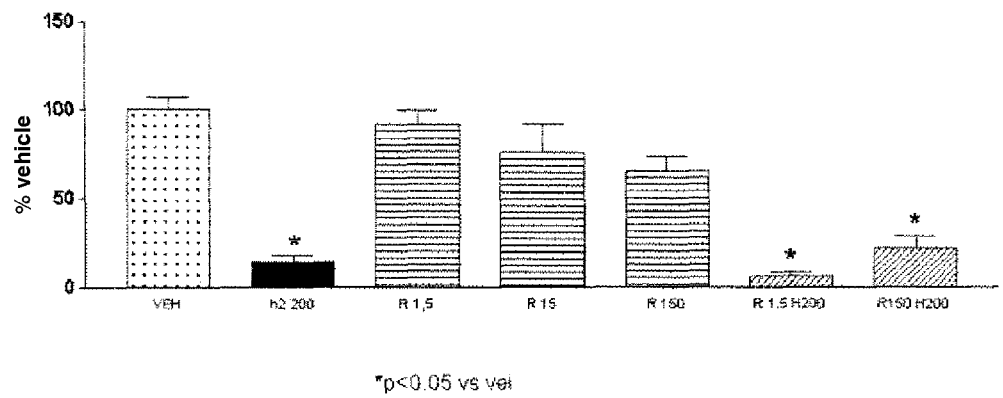
Figure 12:
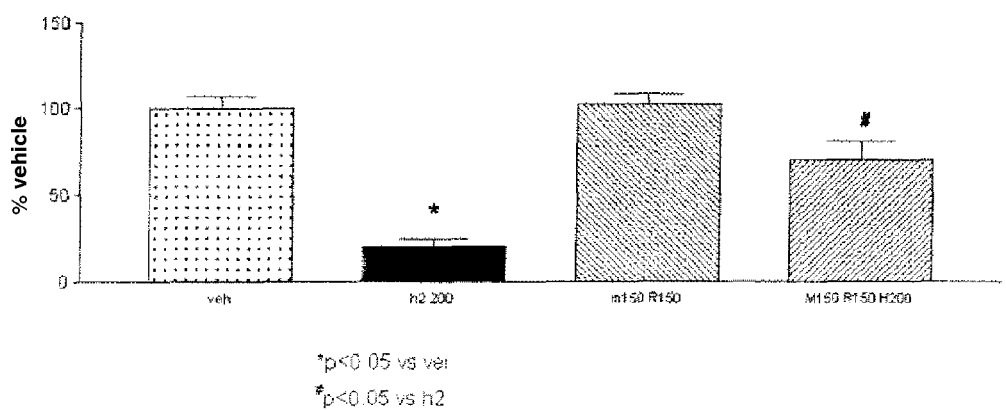

Surprisingly, it has been observed that the mixture of the two extracts, used at lower doses than their respective $EC_{50}$s (10 mcg/ml of rosemary as against its $EC_{50}$ of 15 mcg/ml; and 80 mcg/ml of myrtle as against its $EC_{50}$ of 150 mcg/ml), brings about a reduction of DPPH absorbance which is greater than the summatory effect of the two at the concentrations used (i.e. a 59% reduction of absorbance) but clearly indicating a multiplicative synergistic effect equal to 81% of the reduction of absorbance. (FIG. 6).

The antioxidant capacity of the combination according to the present invention can also be assayed, again in vitro, by testing the effects on the spontaneous motility or motility induced by an electrical stimulus of vascular smooth muscle in the rat, according to the method described here below, and according to the reference models introduced by Mancinelli R. et al., *Functional role of inducible nitric oxide synthase on mouse colonic motility*—Neuroscience Letters, 311: 2, 101-104; (2001); and by Rossetti Z. L. et al., *Biphasic effect of NMDA on the motility of the rat portal vein*—Br. J. Pharmacol. 129: 156-162; (2000)].

Preparation Set-up

The experiments were conducted on isolated portal vein preparations of adult male rats (60-80 g) after anaesthesia with ether.

Segments (4-6 mm) of portal vein were suspended in a bath (15 ml) of Krebs physiological solution maintained at 32° C. and continuously oxygenated with a mixture of $O_2$ 5% and $CO_2$ 5% (pH 7.4). The composition of the Krebs solution was as follows: [mM/1]: NaCl 118, KCl 4.7, $CaCl_2$ 2.52, $MgSO_4$ 1.64, $NaHCO_3$ 24.88, glucose 5.55.

One end of the preparation was anchored to a rigid support placed on the bottom of the bath, while the other end was in contact with an isometric force transducer for recording the spontaneous or electrically stimulated contractile activity.

The preparation was placed between a pair of platinum electrodes connected to a generator of impulses of variable frequency, duration and intensity. Trains of electrical stimuli at 30 Hz, 5 ms duration, with a current intensity of 20-30 mA were applied for a period of 5 s during recording of the contractile activity.

The spontaneous or electrically induced contraction waves were recorded after analog-digital conversion on a computer.

Experimental Protocol

The portal vein segment immediately exhibited spontaneous contractile activity characterised by phasic contraction waves which progressively increased in amplitude.

After a period of adaptation (10-30 min) the waves exhibited virtually stable duration, amplitude and frequency. The preparation was then gradually stretched to establish the optimal length (Lmax) for obtaining the maximum contraction force. This operation was performed by measuring the amplitude of the spontaneous waves at every degree of lengthening (100 μm).

Recordings in Saline Solution. Control Tracings

At Lmax, during the continuous recording of the spontaneous phasic contraction activity, the preparation was periodically stimulated at 5-minute intervals for a period of 35 minutes.

Recordings in the Presence of the Extract or of a Coformulation of Extracts in the Saline Solution Bath 35 minutes after the start of the stimulation cycle, the single extracts (rosemary, myrtle, 200 μg/ml) or combinations of the two extracts [rosemary (200 μg/ml)-myrtle (200 μg/ml)] were added to the saline solution bath. The stimulation cycle was repeated for a period of 35 minutes in the presence of the substances.

Each portal vein was used to assay a single substance or a single combination of substances.

Analysis of the Tracings

The tracings analysed are those obtained by the recordings performed for a period of 35 minutes with the preparation in saline solution (control tracings) and for a subsequent period of 35 minutes in which the preparation was in the presence of single extracts or combinations of extracts (test tracing).

The analysis of the amplitude and frequency of the contraction waves was done at time intervals of 2.5 minutes starting from the beginning of the stimulation cycle for a total period of 35 minutes. In each interval, the mean amplitude±SD of the spontaneous contraction waves was measured as well as the repetition frequency of the waves. The results are reported in FIGS. 7, 8 and 9.

The statistical significance was calculated using analysis of variance (ANOVA) for groups. Data with $p<0.05$ were regarded as significant.

The following examples are provided to illustrate the invention and are not to be regarded as limitative of the scope of the invention.

EXAMPLE 1

500 g of rosemary leaves (*Rosmarinus officinalis*) were separated carefully from the plant and dried naturally for 7 days. 50 g of rosemary were ground and placed in a cellulose thimble.

The thimble was then inserted in the Soxhlet apparatus and subjected to extraction with 400 ml of hexane.

The extraction process was conducted in 10 cycles for a total time period of 6 hours.

After cooling the system, the solution extracted was concentrated with the Rotavapor (c). 2.5 g of dry extract were obtained from 50 g of initial matrix. This will be utilized to make the suitable dilutions to perform our tests.

EXAMPLE 2

2.0 g of dry extract from myrtle leaves (*Myrtus communis*) were obtained according to the same procedure (Soxhlet solid-liquid extraction) described above for the extraction of rosemary, using a water/ethanol solution containing 40% ethanol by weight instead of hexane.

EXAMPLE 3

Results Obtained with the DPPH Method on the Extracts Obtained in Examples 1 and 2, Both Singly and on the Mixture of the Two Reduction of the absorbance of the radical DPPH $6.0 \times 10^{-6}$ M in ethanol was initially evaluated (expressed as percentage reduction as a function of time) in the presence of the standard antioxidant BHA (butylated hydroxyl anisol) at the concentrations of 0.01 mg/ml, 0.1 mg/ml and lastly 1 mg/ml in ethanol (FIG. 1), showing decreases in the absorbance of DPPH of 96.63%, 95.41% and 92.18%, respectively.

After obtaining these 3 standard reference values for the antioxidant potency according to the DPPH spectrophotometric method, the antioxidant potency of the single extracts of rosemary and myrtle obtained in examples 1 and 2, respectively, was then tested.

Increasing doses of myrtle were evaluated (from 0.01 mcg/ml to 3 mcg/ml in ethanol) and a distinct dose-dependent effect was observed in terms of reduction of absorbance of DPPH.

Figure 2:
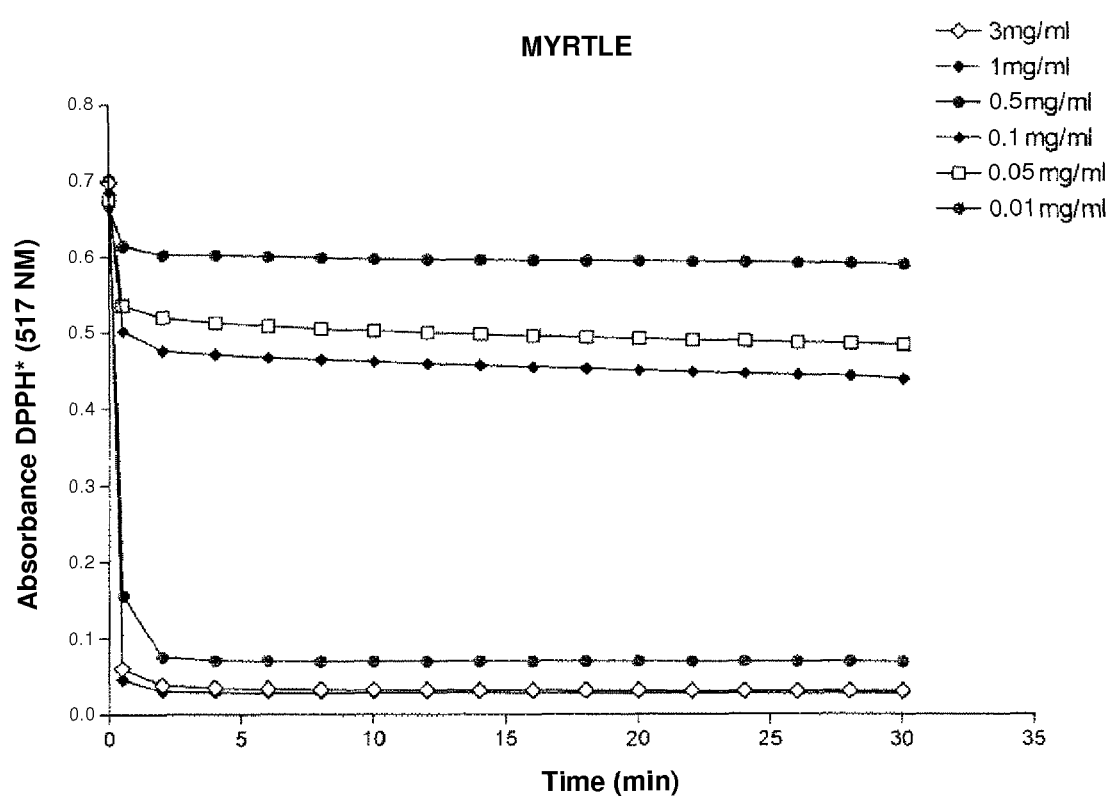
FIG. 2. Antioxidant effect of myrtle at different concentrations. Reduction of absorbance of DPPH* as a function of time in the presence of the myrtle extract at the concentrations listed above.

Myrtle extracted according to the procedure described above (example 2) exerts a distinct antioxidant effect when used at doses greater than 0.5 mcg/ml (FIG. 2).

Figure 3:
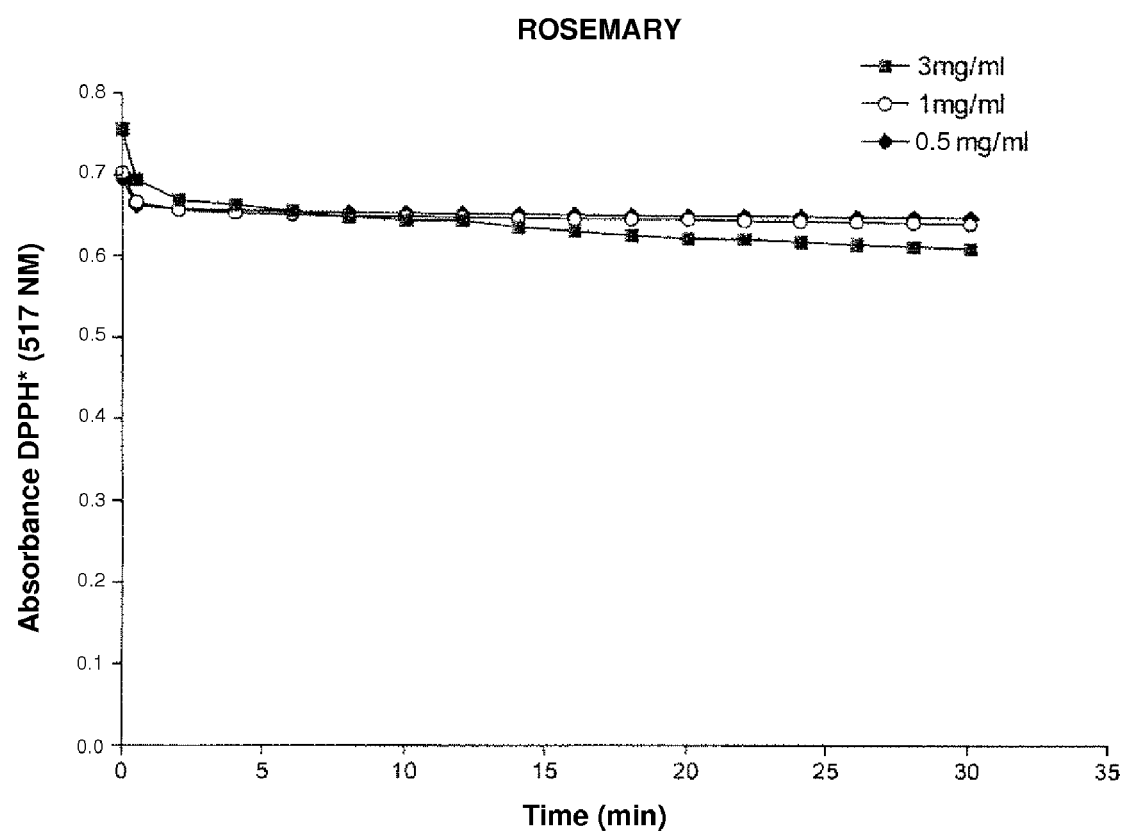
FIG. 3. Antioxidant effect of rosemary at different concentrations. Reduction of absorbance of DPPH* as a function of time in the presence of the aqueous rosemary extract at the concentrations listed above.

By the same token, rosemary extracted according to the procedure described above (example 1) exerts a distinct antioxidant effect, again expressed as a reduction of the absorbance of DPPH, when used at doses greater than 0.5 mcg/ml (FIG. 3).

To better characterise the antioxidant action of each of the two extracts the respective dose concentration at which the single extracts proved capable of inducing 50% inhibition of the absorbance of DPPH (expressed as $EC_{50}$) was identified.

Figure 4:
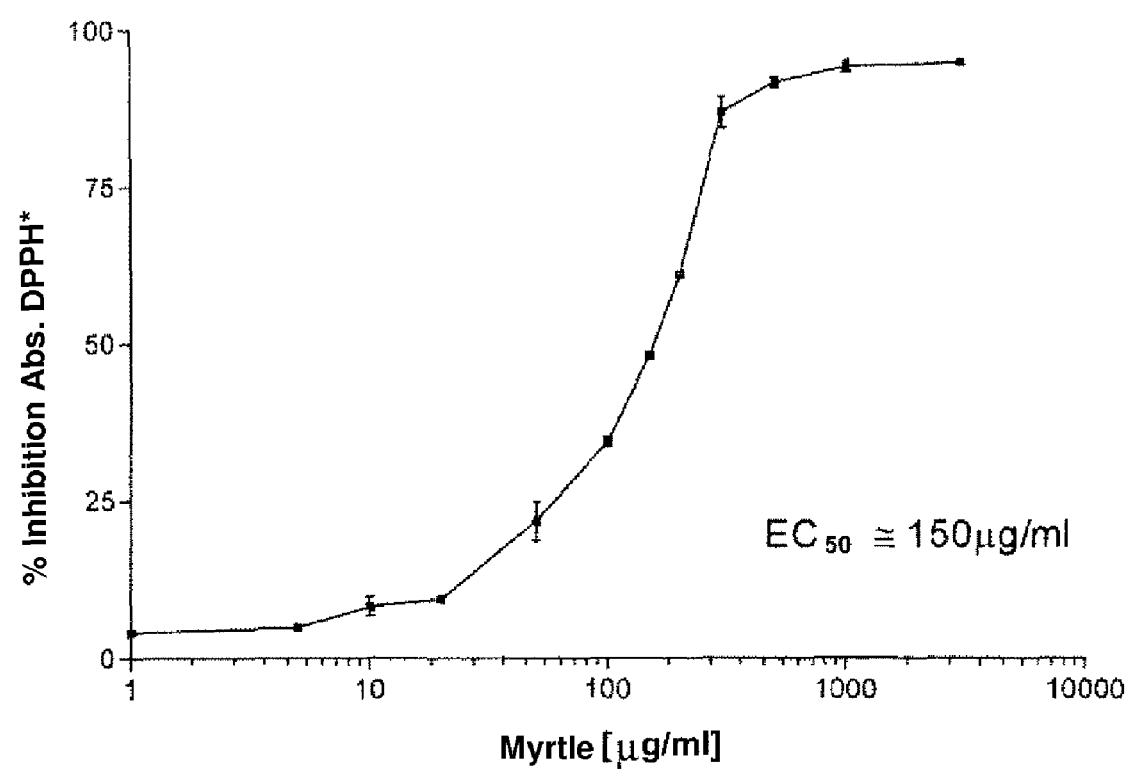
FIG. 4. $EC_{50}$ of myrtle at increasing doses. Antioxidant action at increasing concentrations (1-3000 μg/ml) of the myrtle extract on the free radical DPPH*. The data are expressed as % inhibition of the absorbance of DPPH*.

On testing myrtle at increasing doses (dose range from 1 to 3000 mcg/ml), it was observed that the $EC_{50}$ for myrtle extracted according to the procedure described above is equal to the range 150±10 at a range from 110 to 175 mcg/ml (FIG. 4).

Figure 5:
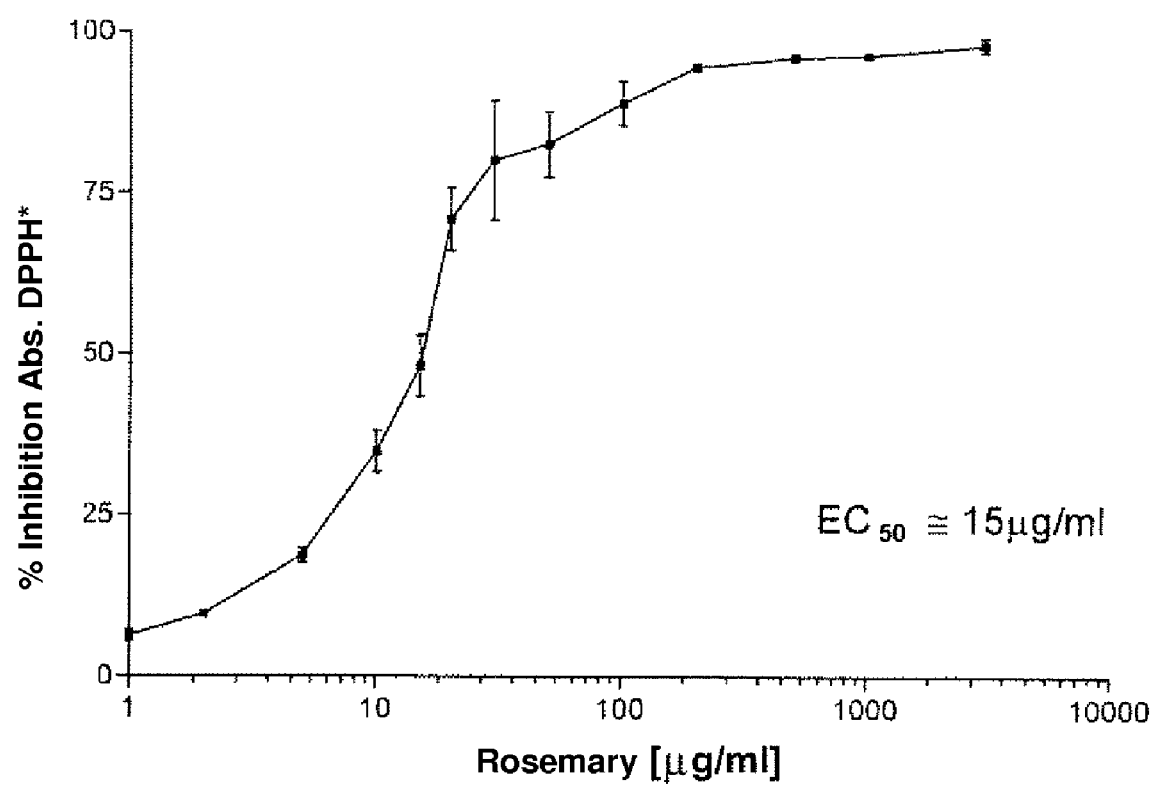
FIG. 5. $EC_{50}$ of rosemary at increasing doses. Antioxidant action at increasing concentrations (1-3000 μg/ml) of the alcoholic rosemary extract on the free radical DPPH*. The data are expressed as % inhibition of the absorbance of DPPH*.

By contrast, for the rosemary extract, also tested at increasing concentrations (ranging from 1 to 3000 mcg/ml), the EC50 was 14±3 at a range from 5 to 35 mcg/ml (FIG. 5).

Lastly, the antioxidant activity of the combination of the two extracts of myrtle and rosemary used synergistically was tested.

Different dosage combinations of the two extracts were thus evaluated and again expressed in terms of their ability to inhibit the absorbance of DPPH.

Surprisingly, it was observed that the mixture of the two extracts, used at doses lower than their respective $EC_{50}$s (10 mcg/ml of rosemary as against its $EC_{50}$ of 15 mcg/ml; and 80 mcg/ml of myrtle as against its $EC_{50}$ of 150 mcg/ml), bring about a reduction of the absorbance of DPPH greater than the simple summatory effect of the two at the concentrations used (i.e. a 65% reduction of absorbance), clearly indicating a multiplicative synergistic effect equal to 81% of the reduction of absorbance (FIG. 6).

This result indicates a surprising, unexpected multiplicative synergistic antioxidant action in the DPPH test of the two extracts of myrtle and rosemary when used together in the same mixture.

The antioxidant potency of the combination of the two appears to be greater than the simple sum of the activities of the two extracts used singly at the same doses.

This unexpected finding thus encourages the use of the combination of extracts of myrtle and rosemary as a dietary supplement, nutraceutical, cosmetic or drug in view of the very substantial dose-dependent antioxidant property of the mixture.

EXAMPLE 4

Results obtained in vitro with extracts of rosemary and myrtle on the spontaneous motility or motility induced by an electrical stimulus of vascular smooth muscle in the rat using the extracts singly and a mixture of the two.

After a period of adaptation, the isolated rat portal vein exhibited phasic contraction waves with an amplitude, duration and frequency oscillating around mean values that remained practically constant for a number of hours.

The electrical stimulation induced an enhancement of the contractile activity which lasted for a space of time of 2-3 minutes following the application of the electrical stimulus.

Motor activity control tracings were recorded for a period of 35 minutes starting from the application of the first electrical stimulation. Subsequently, the electrical stimulus was delivered every 5 minutes for a total number of 6 stimulations.

Effects of Myrtle

The presence of myrtle in the saline solution bath induced an increase in the spontaneous contraction waves (29-30% vs. control) with a concomitant decrease in the repetition frequency (17-25% vs. control). The motility index (MI) trend (FIG. 7) showed interaction between positive inotropic and negative chronotropic effects, resulting in an initial inhibition of the motility with a subsequent slight, non-significant increase in values.

Effects of Rosemary

The presence of rosemary extract [200 μg/ml] in the saline bath induced effects similar to those induced by myrtle. However, the excitatory effect as shown by the MI trend (FIG. 8) was more marked as compared to that obtained with myrtle. It was also observed that the excitatory effects diminish in intensity 20 minutes after administration of the substance.
Effects of the Coformulation of Myrtle [200 μG/ml] and Rosemary [200 μg/ml].

The addition to the saline bath of a mixture of myrtle and rosemary gave rise to an enhancement of vascular motor activity characterised by a marked (p<0.05) increase in MI values (FIG. 9). This increase was already evident in the very first few minutes of recording and remained constant throughout the entire duration of the test. It may be noted that 15 minutes after administration the IM values remain practically stable, indicating that the substance is also capable of controlling the stability of the cellular energy mechanisms involved in the development of the spontaneous activity.

Final Considerations Regarding the Results Obtained

The results of the present experimental investigation indicate that coformulations of the two extracts are surprisingly capable of enhancing, to a statistically significant extent, the effects on motility induced by the substances when administered singly. In particular, the effects induced by the coformulation of myrtle and rosemary appear to be characterised by a marked positive enhancement of muscular inotropism.

This combination substance therefore appears to be indicated in states of hypomotility.

EXAMPLE 5

Results obtained by the combined administration of dry extracts of myrtle and rosemary on apoptosis induced by exposure of rat pheochromocytoma PC-12 cell cultures to $H_2O_2$.

The test used was the ATPLite™ test (Perkin Elmer, Milan), an ATP monitoring system based on luciferase, which permits assessment of the cytostatic and proliferative effects of various biological compounds. [Cree I. A. and Andreotti P. E. *Measurement of cytotoxicity by ATP-based luminescence assay in primary cell cultures and cell lines*—Toxicology in Vitro, 11, 553-556; (1997); Guan S., Bao Y. M., Jiang B., An L. *Protective effect of protocatechuic acid from Alpinia oxyphylla on hydrogen peroxide-induced oxidative PC12 cell death*—Eur. J. Pharmacol. 24: 538; (2006)].

The rat pheochromocytoma PC12 cell line (European Collection of Cell Cultures—ECACC, Sigma Aldrich, Milan) was used to evaluate the potential protective effects of extracts of rosemary (the same extract as described above in example 1) and of myrtle (the same extract as described above in example 2) against the toxicity induced by hydrogen peroxide ($H_2O_2$). The cells were grown on 96-well plates treated with poly-D-lysine (Sigma Aldrich, Milan) in D-MEM culture medium added with fetal bovine serum (FBS), penicillin/streptomycin, gentamycin, L-glutamine (all Invitrogen, Milan). The cells were pre-exposed for 1 hour to various concentrations of extracts of rosemary and myrtle (from 1.5 to 300 µg/500 µl) and then to $H_2O_2$ 200 µM. After 24 hours the activity of the extracts on ATP production was evaluated using a Victor 3 spectrophotometer (Perkin Elmer, Milan). The statistical analysis was done using the Graph-Pad Prism program (San Diego, USA).

As shown in Figure A, $H_2O_2$ 200 µM (h2 200) used without addition of extracts, gives rise to a significant reduction of ATP production (−80%±4.1 vs vehicle (veh)) in the PC12 cells compared to the control group (veh). The myrtle extract in itself induces a significant increase in ATP production at the concentration of 300 µg/500 µl (myr 300) (+78%±22 vs. vehicle), but is not capable of protecting the cells against the toxicity induced by $H_2O_2$, at the various concentrations (myr 1.5-300 h2).

As shown in Figure B, the rosemary extract, at the various concentrations tested, is not capable of protecting the PC12 cells against the $H_2O_2$-induced stress. This extract, moreover, shows in itself (R) a non-significant tendency to reduce ATP production.

As shown in Figure C, the combination of the extracts of myrtle and rosemary, at concentrations per se inactive (M 150 and R 150), is capable of protecting the PC12 cells against the ATP reduction induced by $H_2O_2$ 200 µM (+250%±22.3 vs. $H_2O_2$).

In conclusion, the results of this experimentation have surprisingly demonstrated that the combination of the two extracts is capable of significantly protecting rat PC12 cells against the apoptotic process (as expressed by ATP reduction) induced by hydrogen peroxide.

This synergistic effect is all the more surprising in the light of the diametrically opposite (pro-apoptotic) effect exerted by one of the two extracts (rosemary) when administered separately in the same dosage range.

EXAMPLE 6

The following formulations were prepared using the extracts indicated in examples 1, 2, 3 and 4 according to the following preparation modalities and at the following doses for the single components:

1) 500 mg tablet containing 100 mg rosemary dry extract ¼; 100 mg myrtle dry extract ¼; 1.77 mg vitamin B1; 1.6 mg vitamin B2; 18 mg nicotinamide; 6.55 mg vitamin B5; 2.42 mg vitamin B6; 10 mg CoQ10; 244.66 mg cellulose; 10 mg silica; 5 mg stearate.
2) 850 mg tablet containing 100 mg rosemary dry extract ¼; 100 mg myrtle dry extract ¼; 192.5 mg glucosamine; 50 mg curcuma; 60 mg vitamin C; 100 mg chondroitin sulphate; 20 mg silica; 10 mg stearate.
3) 500 mg tablet containing 100 mg rosemary dry extract ¼; 100 mg myrtle dry extract ¼; 50 mg gingko biloba dry extract 24%; 50 mcg folic acid; 5.5. mg selenium methionine; 62.5 mg zinc gluconate 12%; 100 mg heavy magnesium oxide; 50 mg phosphadylserine 20%; 16.95 mg cellulose; 10 mg silica; 5 mg stearate.
4) 500 mg tablet containing 60 mg rosemary dry extract ¼, 100 mg myrtle dry extract ¼, 8 mg lutein 25%; 4 mg zeaxanthine; 300 mg vitamin E; 23 mg cellulose; 10 mg of silica; 5 mg of stearate.
5) 500 mg tablet containing 100 mg rosemary dry extract ¼; 100 mg myrtle dry extract ¼; 10 mg helichrysum dry extract ¼; 50 mg curcuma; 100 mg alpha-lipoic acid; 60 mg vitamin C; 50 mg cellulose; 20 mg silica; 10 mg stearate.
6) 500 mg tablet containing 150 mg rosemary dry extract ¼; 50 mg myrtle dry extract ¼; 20 mg CoQ10; 220 mg hawthorn dry extract 1% vitexin; 30 mg cellulose; 20 mg silica; 10 mg stearate.
7) 850 mg tablet containing 150 mg rosemary dry extract ¼; 150 mg myrtle dry extract ¼; 500 mg omega 3 fatty acids EPA and DHA (minimum 60% concentration, EPA:DHA ratio 2:1), 5 mg hydroxytyrosol; 30 mg cellulose; 10 mg silica; 5 mg stearate.
8) 500 mg tablets containing 150 mg rosemary dry extract ¼; 150 mg myrtle dry extract ¼; 10 mg helichrysum dry extract ¼; 5 mg hydroxytyrosol; 62.5 mg zinc gluconate 12%; 100 mg heavy magnesium oxide; 17.5 mg cellulose; 10 mg silica; 5 mg stearate.
9) 500 mg tablets containing 50 mg rosemary dry extract ¼; 50 mg myrtle dry extract ¼; 300 mg acetyl-L-carnitines; 10 mg CoQ10; 5 mg hydroxytyrosol; 62.5 mg zinc gluconate 12%; 7.5 mg cellulose; 10 mg silica; 5 mg stearate.

What is claimed is:

1. A composition consisting essentially of:
   a) from approximately 1 mg to 1000 mg of an extract of myrtle (*Myrtus communis*) produced starting from the leaves of the myrtle by solid/liquid extraction;
   b) from approximately 1 mg to 1000 mg of an extract of rosemary (*Rosmarinus officinalis*) produced by starting from the leaves of the rosemary by solid/liquid extraction; and c) therapeutically effective amounts of glucosamine, curcuma and chondroitin; wherein, the combination of a) and b) has an antioxidant potency at least 5% greater than the sum of the antioxidant potencies of a) and b) as single extracts, as measured with the 2,2-diphenyl-1-picryl-hydrazyl (DPPH) test.

2. The composition of claim 1, wherein the combination has a potency of 15% or more higher than the sum of the single extracts of myrtle and rosemary.

3. The composition of claim 1, wherein the extract of myrtle is produced starting from dried leaves and has a reference antioxidant action observed with the DPPH test and expressed as the ability to inhibit the absorbance of DPPH by 50% ($EC_{50}$) at concentrations ranging from 110 to 175 mcg/ml;
   wherein the extract of rosemary is produced starting from dried leaves and has a reference antioxidant action observed with the DPPH test and expressed as $EC_{50}$ at concentrations ranging from 5 to 35 mcg/ml.

4. The composition of claim 1, in which the (a):(b) ratio weight-by-weight ranges from 0.1:1000 to 1000:0.1 for myrtle and rosemary, respectively.

5. The composition of claim 1, in a form selected from the group consisting of solid, semisolid, liquid form, tablets, lozenges, pills, capsules, granules, syrups, ampoules, drops, emulsions, suspensions, creams and gels.

6. The composition of claim 1, wherein the antioxidant potency of the combination is higher than that of the single extracts of rosemary and myrtle by about 15% to about 50%.

7. The composition of claim 1, in a form selected from the group consisting of dietary supplement, parenteral, rectal, transdermal, and topical.

8. A composition consisting essentially of:
a) from approximately 1 mg to 1000 mg of extract of myrtle (*Myrtus communis*) produced starting from the leaves of myrtle by solid/liquid extraction;
b) from approximately 1 mg to 1000 mg of extract of rosemary (*Rosmarinus officinalis*) produced starting from the leaves of rosemary by solid/liquid extraction; and
c) therapeutically effective amounts of helichrysum and curcuma;
wherein, the combination of a) and b) has an antioxidant potency at least 5% greater than the sum of the antioxidant potencies of a) and b) as single extracts, as measured with the 2,2-diphenyl-1-picryl-hydrazyl (DPPH) test.

9. A composition consisting essentially of:
a) from approximately 1 mg to 1000 mg of extract of myrtle (*Myrtus communis*) produced starting from the leaves of myrtle by solid/liquid extraction;
b) from approximately 1 mg to 1000 mg of extract of rosemary (*Rosmarinus officinalis*) produced starting from the leaves of rosemary by solid/liquid extraction; and
c) therapeutically effective amounts of CoQ10 and hawthorn;
wherein, the combination of a) and b) has an antioxidant potency at least 5% greater than the sum of the antioxidant potencies of a) and b) as single extracts, as measured with the 2,2-diphenyl-1-picryl-hydrazyl (DPPH) test.

10. A process of making the composition of claim 1, 8 or 9, in which the leaves of said rosemary and myrtle are subjected to solid/liquid extraction according to a method to be selected from the group consisting of: Soxhlet extraction, maceration, percolation, ultrasound, vapour distillation, and extraction with supercritical fluids, said forms of extraction being conducted using a vegetal matrix: solvent (weight-by-weight) ratio ranging from 1:1 to 1:50 and for time periods ranging from 30 minutes to 45 days in a solvent selected from the group consisting of: water, hydroalcoholic solutions, polar organic solvents, apolar aprotic organic solvents and carbon dioxide.

11. The process of claim 10, in which the leaves of rosemary or myrtle are ground before being subjected to extraction.

12. The process of claim 10, in which the final extract obtained at the end of claim 9 is subjected to further extraction.

13. The process of claim 10, wherein the polar organic solvents are selected from the group consisting of alcohols, ketones, ethers, esters, and methylene chloride.

14. The process of claim 10, wherein said esters are selected from the group consisting of acetone, ethylene glycol, propylene glycol, diethylether, petroleum ether, and ethyl acetate.

15. The process of claim 10, wherein the apolar aprotic organic solvents are hydrocarbon solvents.

* * * * *